US 6,669,624 B2

(12) United States Patent
Frazier (10) Patent No.: US 6,669,624 B2
(45) Date of Patent: Dec. 30, 2003

(54) TEMPORARY HEART-ASSIST SYSTEM (76) Inventor: O. Howard Frazier, c/o J. F. Brazos Enterprises, Ltd./1402 Bonnie Brae, Houston, TX (US) 77006

( * ) Notice: Subject to any disclaimer, the term of this patent is extended or adjusted under 35 U.S.C. 154(b) by 0 days.

(21) Appl. No.: 10/106,744

(22) Filed: Mar. 26, 2002

(65) Prior Publication Data

US 2003/0191357 A1 Oct. 9, 2003

(51) Int. Cl.[7] .............................................. A61M 1/10
(52) U.S. Cl. .................... 600/18; 623/3.26; 623/3.28
(58) Field of Search ...................... 600/16–18; 623/3.26, 623/3.28

(56) References Cited

U.S. PATENT DOCUMENTS

| | | | |
|---|---|---|---|
| 4,261,339 A | 4/1981 | Hanson et al. ............... 128/1 D |
| 4,311,133 A | 1/1982 | Robinson .................... 128/1 D |
| 4,327,709 A | 5/1982 | Hanson et al. ............... 128/1 D |
| 4,346,698 A | 8/1982 | Hanson et al. ............... 128/1 D |
| 4,362,150 A | 12/1982 | Lombardi, Jr. et al. ..... 128/1 D |
| 4,397,617 A | 8/1983 | Sergio et al. ................ 417/475 |
| 4,402,307 A | 9/1983 | Hanson et al. ............... 128/1 D |
| 4,444,186 A | 4/1984 | Wolvek et al. ............... 128/325 |
| 4,467,790 A | 8/1984 | Schiff ......................... 128/1 D |
| 4,473,067 A | 9/1984 | Schiff ......................... 128/1 D |
| 4,522,194 A | 6/1985 | Normann ..................... 128/1 D |
| 4,524,466 A | 6/1985 | Hall et al. ....................... 603/3 |
| 4,531,512 A | 7/1985 | Wolvek et al. ............... 128/1 D |
| 4,531,936 A | 7/1985 | Gordon ......................... 604/49 |
| 4,552,127 A | 11/1985 | Schiff ......................... 128/1 D |
| 4,576,142 A | 3/1986 | Schiff ......................... 128/1 D |
| 4,644,936 A | 2/1987 | Schiff ......................... 128/1 D |
| 4,697,574 A | 10/1987 | Karcher et al. ............. 128/1 D |
| 4,733,652 A | 3/1988 | Kantrowitz et al. ........ 128/1 D |
| 4,804,358 A | 2/1989 | Karcher et al. ................ 600/17 |
| 4,809,681 A * | 3/1989 | Kantrowitz et al. .......... 600/17 |
| 4,822,357 A | 4/1989 | Forster et al. .................. 623/3 |
| 4,897,077 A | 1/1990 | Cicciu et al. .................. 600/18 |
| 4,901,707 A | 2/1990 | Schiff ......................... 128/1 D |
| 4,968,293 A | 11/1990 | Nelson ........................ 600/16 |
| 4,994,018 A | 2/1991 | Saper ........................... 600/18 |
| 5,158,529 A | 10/1992 | Kanai ........................... 600/18 |
| 5,195,942 A | 3/1993 | Weil et al. .................... 600/18 |
| 5,230,692 A | 7/1993 | Kanai ........................... 600/18 |
| 5,263,979 A | 11/1993 | Isoyama et al. ................. 623/3 |
| 5,330,451 A | 7/1994 | Gabbay ........................ 604/284 |
| 5,344,443 A | 9/1994 | Palma et al. ..................... 623/3 |
| 5,413,558 A | 5/1995 | Paradis ........................ 604/101 |
| RE34,993 E | 7/1995 | Cicciu et al. .................. 600/18 |
| 5,443,503 A | 8/1995 | Yamane ........................... 623/3 |
| 5,456,665 A | 10/1995 | Postell et al. ................. 604/96 |
| 5,460,607 A | 10/1995 | Miyata et al. ................. 604/96 |
| 5,524,757 A | 6/1996 | Andrews et al. ............. 206/417 |
| 5,588,812 A | 12/1996 | Taylor et al. ................. 417/356 |
| 5,599,329 A | 2/1997 | Gabbay ........................ 604/284 |
| 5,618,270 A | 4/1997 | Orejola ........................ 604/164 |
| 5,632,771 A | 5/1997 | Boatman et al. ................. 623/1 |

(List continued on next page.)

Primary Examiner—George R. Evanisko
(74) Attorney, Agent, or Firm—Tim Headley; Gardere Wynne Sewell LLP (57) ABSTRACT A balloon is positionable in the patient's descending aorta. The balloon includes a balloon catheter and two pressure sensors that electrically couple to an extra-corporeal controller. The balloon itself also couples pneumatically to the extra-corporeal controller. An extra-corporeal pump electrically couples to the extra-corporeal controller, the pump having an outlet connectable to the patient's infra-diaphragmatic The pump inlet is connectable via a cannula to the patient's supra-diaphragmatic artery. artery. A doctor inserts the balloon into the descending aorta, and positions the balloon near the level of the patient's diaphragm. A balloon catheter, coupled to the extra-corporeal controller, inflates and deflates the balloon. An electrocardiogram ECG and proximal aortic blood pressure, measured in the upper arterial compartment via a lumen in the balloon catheter, serve as inputs to cycle the balloon synchronously with the heartbeat.

11 Claims, 9 Drawing Sheets

U.S. PATENT DOCUMENTS

| | | | |
|---|---|---|---|
| 5,683,347 A | 11/1997 | Miyata et al. | 600/18 |
| 5,697,906 A | 12/1997 | Ariola et al. | 604/96 |
| 5,718,861 A | 2/1998 | Andrews et al. | 264/235 |
| 5,759,175 A | 6/1998 | Ariola et al. | 604/96 |
| 5,772,631 A | 6/1998 | Lepor | 604/96 |
| 5,782,847 A | 7/1998 | Plaia et al. | 606/159 |
| 5,817,001 A | 10/1998 | Leschinsky et al. | 600/18 |
| 5,865,721 A | 2/1999 | Andrews et al. | 600/18 |
| 5,913,814 A | 6/1999 | Zantos | 600/18 |
| 5,928,132 A | 7/1999 | Leschinsky | 600/16 |
| 5,935,501 A | 8/1999 | Andrews et al. | 264/250 |
| 6,015,434 A | 1/2000 | Yamane | 623/3 |
| 6,024,693 A | 2/2000 | Schock et al. | 600/18 |
| 6,099,460 A | 8/2000 | Denker | 600/17 |
| 6,149,578 A | 11/2000 | Downey et al. | 600/18 |
| 6,149,681 A | 11/2000 | Houser et al. | 623/1.12 |
| 6,149,683 A | 11/2000 | Lancisi et al. | 623/3 |
| 6,191,111 B1 | 2/2001 | Leschinsky | 514/12 |
| 6,200,260 B1 | 3/2001 | Bolling | 600/16 |
| 6,210,319 B1 | 4/2001 | Williams et al. | 600/18 |
| 6,213,975 B1 | 4/2001 | Laksin | 604/103.13 |
| 6,238,334 B1 | 5/2001 | Easterbrook, III et al. | 600/16 |
| 6,238,382 B1 | 5/2001 | Schock et al. | 604/533 |
| 6,241,706 B1 | 6/2001 | Leschinsky et al. | 604/99 |
| 6,245,008 B1 | 6/2001 | Leschinsky et al. | 600/18 |
| 6,248,086 B1 | 6/2001 | Sweezer et al. | 604/4.01 |
| 6,254,563 B1 | 7/2001 | Macoviak et al. | 604/8 |
| 6,290,641 B1 | 9/2001 | Nigroni et al. | 600/18 |
| 6,299,575 B1 | 10/2001 | Bolling | 600/16 |

\* cited by examiner

TEMPORARY HEART-ASSIST SYSTEM

FIELD OF THE INVENTION

The present invention relates generally to methods and devices for mechanically assisting the failing heart. More specifically, it relates to balloon catheters and bypass pumps.

BACKGROUND OF THE INVENTION

Many types of cardiac assist devices have been developed over the past 40 years. The general types of devices can be characterized as short-term (hours to days), bridge-to-transplantation, bridge-to-recovery, and permanent or long-term. The goal of these devices is to mechanically support the failing heart by increasing systemic perfusion, and/or reducing the workload of the failing heart, thus creating the most favorable environment for cardiac recovery.

Short-term devices are used on patients whose hearts have sustained a serious injury but can recover if adequately supported. The most commonly used short-term device is the intra-aortic balloon pump ("IABP"). Indications for employment of the IABP include cardiogenic shock or severe heart failure secondary to acute myocardial infarction or following open-heart surgery, unstable angina resistant to drug therapy, and refractory ventricular irritability after myocardial infarction. The following patents disclose intra-aortic balloon pumps. The full disclosures of these patents are all incorporated herein by this reference:

| | |
|---|---|
| 6,290,641 | Intra-aortic balloon pump having improved automated electrocardiogram based intra-aortic balloon deflation timing |
| 6,245,008 | Fast response intra-aortic balloon pump |
| 6,241,706 | Fast response intra-aortic balloon pump |
| 6,238,382 | Intra-aortic balloon catheter having a tapered Y-fitting |
| 6,210,319 | Intra-aortic balloon pump condensation prevention system |
| 6,191,111 | Method and device for enhancing of biobypass by increasing the coronary blood flow |
| 5,817,001 | Method and apparatus for driving an intra-aortic balloon pump |

The following patents disclose intra-aortic balloons. The full disclosures of these patents are all incorporated herein by this reference:

| | |
|---|---|
| 6,213,975 | Intra-aortic balloon catheter having an ultra-thin stretch blow molded balloon membrane |
| 6,149,578 | Piston-action intra-aortic coronary assist device |
| 6,024,693 | Intra-aortic balloon catheter |
| 5,935,501 | Method for making a packaging sheath for intra-aortic balloon catheters |
| 5,928,132 | Closed chest intra-aortic balloon based ventricular assist device |
| 5,913,814 | Method and apparatus for deflation of an intra-aortic balloon |
| 5,865,721 | Intra-aortic balloon catheters |
| 5,817,001 | Method and apparatus for driving an intra-aortic balloon pump |
| 5,772,631 | Procedure for alleviating arterial obstruction |
| 5,759,175 | Intra-aortic balloon catheter |
| 5,718,861 | Method of forming intra-aortic balloon catheters |
| 5,697,906 | Intra-aortic balloon catheter |
| 5,683,347 | Balloon catheter |
| 5,618,270 | Transthoracic aortic sleeve |
| 5,599,329 | Multi purpose perfusion cannula |
| 5,524,757 | Packaging sheaths for intra-aortic balloon catheters |
| 5,460,607 | Balloon catheter |
| 5,456,665 | Intra-aortic balloon catheter |
| RE34,993 | Method of inserting a lab device into the body |
| 5,413,549 | Devices and methods for efficient intra-aortic balloon pumping |
| 5,330,451 | Multi purpose perfusion cannula |
| 5,230,692 | Intra-aortic balloon pump |
| 5,158,529 | Pumping device for operating an intra-aortic balloon |
| 5,120,299 | Intra-aortic balloon assembly with hemostasis device |
| 4,994,018 | Intra-aortic balloon assembly |
| 4,901,707 | Prepackaged intra-aortic balloon assembly with holder, and method of using same |
| 4,897,077 | Method of inserting an IAB device into the body |
| 4,827,906 | Apparatus and method for activating a pump in response to optical signals from a pacemaker |
| 4,809,681 | Electrocardiographic measurement method for controlling an intra-aortic balloon pump |
| 4,804,358 | Coronary perfusion pump |
| 4,733,652 | Intra-aortic balloon |
| 4,697,573 | Percutaneous intra-aortic balloon and method for using same |
| 4,644,936 | Percutaneous intra-aortic balloon and method for using same |
| 4,576,142 | Percutaneous intra-aortic balloon and method for using same |
| 4,552,127 | Percutaneous intra-aortic balloon having an EKG electrode and a twisting stylet for coupling the EKG electrode to monitoring and/or pacing instrumentation external to the body |
| 4,531,512 | Wrapping system for intra-aortic balloon utilizing a wrapping envelope |
| 4,522,195 | Apparatus for left heart assist |
| 4,522,194 | Method and an apparatus for intra-aortic balloon monitoring and leak detection |
| 4,515,587 | IAB having apparatus for assuring proper balloon inflation and deflation |
| 4,473,067 | Introducer assembly for intra-aortic balloons and the like incorporating a sliding, blood-tight seal |
| 4,467,790 | Percutaneous balloon |
| 4,444,186 | Envelope wrapping system for intra-aortic balloon |
| 4,422,447 | Percutaneous balloon |
| 4,407,271 | Apparatus for left heart assist |
| 4,402,307 | Balloon catheter with rotatable energy storing support member |
| 4,362,150 | Percutaneous intra-aortic balloon apparatus |
| 4,346,698 | Balloon catheter with rotatable support |
| 4,327,709 | Apparatus and method for the percutaneous introduction of intra-aortic balloons into the human body |
| 4,311,133 | Intra-aortic balloon |
| 4,287,892 | Cannula for intra-aortic balloon devices and the like |
| 4,276,874 | Elongatable balloon catheter |
| 4,261,339 | Balloon catheter with rotatable support |
| 4,122,858 | Adapter for intra-aortic balloons and the like |
| 4,080,958 | Apparatus for aiding and improving the blood flow in patients |
| 3,985,123 | Method and means for monitoring cardiac output |

Aortic occlusion balloons are known in the prior art. Such aortic balloons are non co-pulsating with the heartbeat and are not employed with an aortic bypass pump. The following patents disclose aortic occlusion balloons. The full disclosures of these patents are all incorporated herein by this reference:

| | |
|---|---|
| 6,254,563 | Perfusion shunt apparatus and method |
| 6,248,086 | Method for cannulating a patient's aortic arch and occluding the patients ascending aortic arch |
| 5,413,558 | Selective aortic perfusion system for use during CPR |
| 5,216,032 | Selective aortic arch perfusion using perfluorochemical and alpha-adrenergic agonist to treat cardiac arrest |
| 5,195,942 | Cardiac arrest treatment |
| 4,697,574 | Pump for assistance in circulation |
| 4,531,936 | Device and method for the selective delivery of drugs to the myocardium |

The basic components of the intra-aortic balloon pump ("IABP") are a catheter tipped with a long balloon and a pump console that shuttles helium gas through the catheter to inflate and deflate the balloon synchronously with the heart beat. The balloon is inserted into an artery and guided to a position in the descending thoracic aorta just distal to the left subclavian artery. The pump control console contains signal processing, drive, timing, and control mechanisms for appropriate inflation and deflation. During cardiac systole ventricular contraction and ejection, the IABP is rapidly deflated, reducing the workload and oxygen demands of the heart by decreasing the resistance to blood flow from the ventricle. During cardiac diastole ventricular relaxation and filling, the IABP is rapidly inflated counter-pulsation increasing aortic and coronary perfusion pressures. Timing of the inflation-deflation cycle is based on the electrocardiogram and arterial blood pressure waveform.

When heart failure is severe, the IABP cannot provide adequate circulatory support because it cannot replace cardiac function. The treatment of severe heart failure requires the use of cardiac-bypass blood pumps. These devices are more invasive than the IABP and employ direct cannulation of the ventricle or atrium. Implantation and removal of the cardiac cannulas may further injure the heart and be associated with bleeding complications. It is estimated that nearly 100,000 patients worldwide underwent short-term mechanical circulatory support during 2000. The following patents disclose cardiac bypass pumps. The full

| | |
|---|---|
| 6,238,334 | Method and apparatus for assisting a heart to pump blood |
| 6,149,683 | Power system for an implantable heart pump |
| 6,099,460 | Electromagnetic heart-assist technique and apparatus |
| 6,015,434 | Artificial heart pump |
| 5,588,812 | Implantable electric axial-flow blood pump |
| 5,443,503 | Artificial heart pump |
| 5,344,443 | Heart pump |
| 5,263,979 | Artificial heart |
| 4,822,357 | Auxiliary artificial heart |
| 4,524,466 | Continuous rotation reversible pitch axial thrust heart pump |
| 4,397,617 | Heart pump for the circulation of blood outside the body of a living subject |
| 4,310,930 | Rigid-vane artificial heart |

Aortic bypass pumps are known in the prior art. Aortic bypass pumps are not employed with a co-pulsating aortic occlusion balloon for heart assistance. The following patents disclose aortic bypass pumps. The full disclosures of these patents are all incorporated herein by this reference:

| | |
|---|---|
| 6,299,575 | Implantable heart assist system |
| 6,200,260 | Implantable heart assist system |
| 5,749,855 | Catheter pump |
| 4,968,293 | Circulatory assist device |

Because of the limitations of aortic bypass pumps, intra-aortic balloon pumps, and the complications associated with cardiac bypass pumps, there is a need for an improved short-term heart-assist device.

SUMMARY OF THE INVENTION

A preferred embodiment of the present invention provides a method and a system to temporarily assist the failing heart. The temporary heart-assist system comprises an occluding device positionable in the patient's descending aorta. The occluding device may or may not include a pressure sensor that electrically couples to an extra-corporeal controller. The occluding device itself also couples pneumatically to the extra-corporeal controller. The pump inlet of an extra-corporeal pump is connectable via a cannula to a patient's supra-diaphragmatic artery. The pump outlet of the extra-corporeal pump is connectable via a cannula to a patient's infra-diaphragmatic artery.

In the method of the present invention, a doctor inserts into the patient the occluding device via a peripheral artery into the descending aorta, and positions the occluding device near the level of the patient's diaphragm. The occluding device catheter, coupled to the extra-corporeal controller, inflates and deflates the occluding device. The electrocardiogram ECG and proximal aortic blood pressure, measured in the upper arterial compartment via a lumen in the occluding device catheter, serve as inputs to cycle the occluding device synchronously with the heartbeat. The step of inflating occurs just prior to the start of cardiac systole co-pulsation and ventricular ejection. The extra-corporeal pump continuously or cyclically pumps blood from a supra-diaphragmatic artery to a infra-diaphragmatic artery. The pumping flow rate varies in response to the end-systolic pressure measured in the upper arterial compartment of the patient's body. The step of deflating the aortic balloon occurs at the start of cardiac diastole and aortic valve closure. Deflating the balloon stabilizes the perfusion pressure between the upper and lower arterial compartments.

In another feature of the present invention, the method of the present invention pumps blood from the patient's upper to the patient's lower arterial compartments.

The present invention is designed to temporarily assist the failing human heart for a period of several hours to several days. The objectives of the heart-assist system of the present invention are to augment cardiac output and enhance systemic perfusion, reduce the workload and oxygen requirements of the acutely failing heart and allow for its recovery, allow for optimization of concomitant drug therapy, require minimal surgical intervention for insertion and removal, and reduce additional trauma to the failing heart by eliminating a need for direct cannulation of the left atrium or left ventricle. An additional feature of this technology is enhancement of diastolic perfusion by elevation of pressure throughout the diastolic interval and, unlike a commercially available balloon pump, enhancement of perfusion to all organs.

The present invention allows for treatment of the failing heart in a minimally invasive manner with augmentation of left ventricular stoke volume cardiac output and simultaneous reduction in left ventricular workload and oxygen requirements of the heart.

An important feature of the invention is that it rapidly inflates a small-volume balloon, partially occluding the aorta just prior to the start of cardiac systole and ventricular ejection. In another feature of the invention, it regulates aorta-aorta bypass blood pump flow to obtain a specific end-systolic aortic pressure measured in the upper arterial compartment. In another feature of the invention, decreasing end-systolic aortic pressure results in an increased ventricular stroke volume based on the ventricular pressure-volume-contractility relationship. Decreased systolic pressure also reduces the workload on the failing heart. Increased bypass pump blood flow elevates perfusion pressure in the lower arterial compartment. In another feature of the invention, during ventricular diastole, the system rapidly deflates an aortic balloon at end-systole. Deflating the aortic balloon stabilizes the perfusion pressure between the upper and lower arterial compartments.

DETAILED DESCRIPTION

Figure 1:
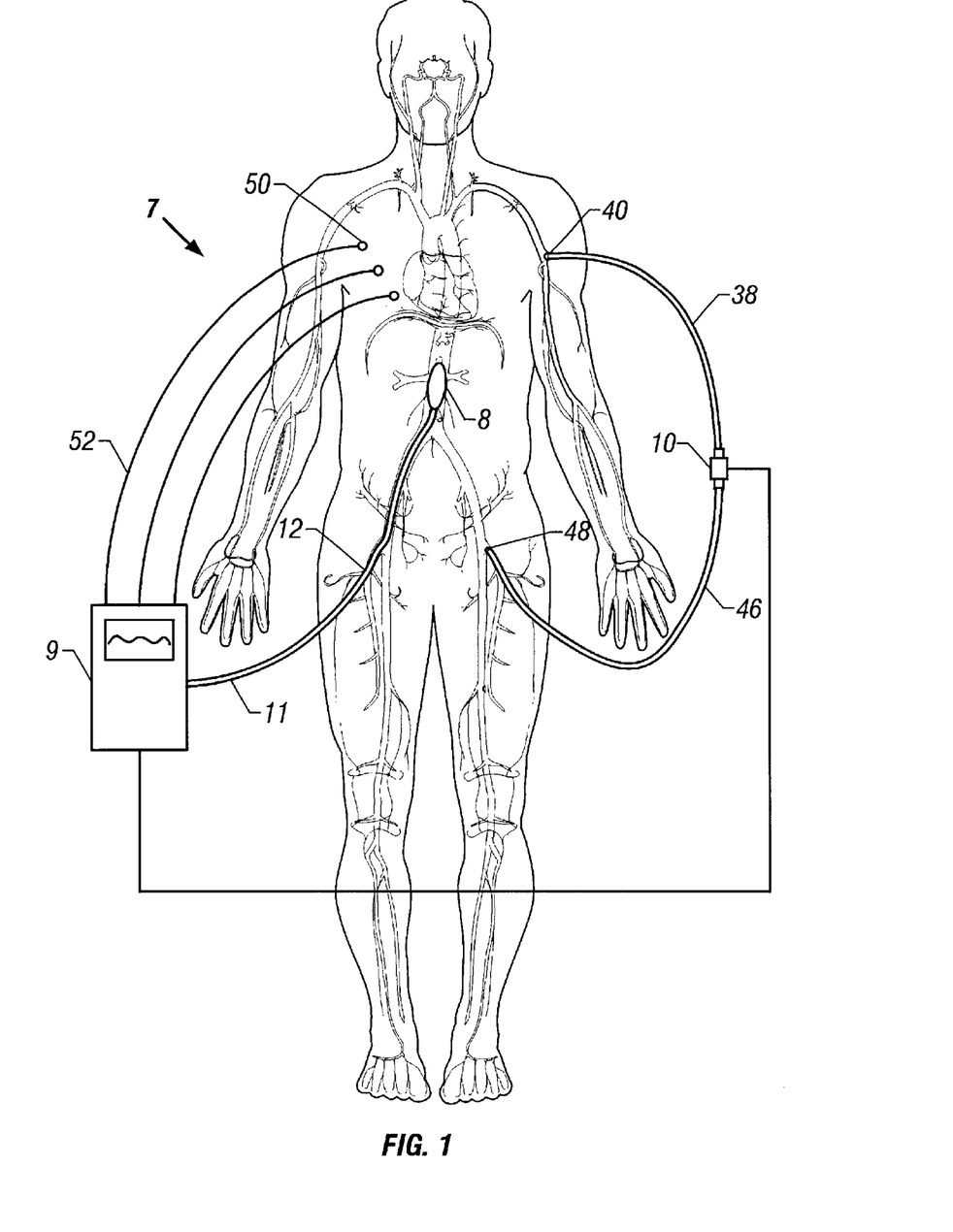
FIG. 1 depicts an overview of the temporary heart-assist system, illustrating the intra-aortic balloon, aortic-aortic external bypass pump, and external controller, as installed on a patient.

In the drawings, like numerals designate like parts throughout the drawings. In FIG. 1, a temporary heart-assist system 7 is illustrated in use with a human heart. The heart-assist system 7 includes an occluding device, or balloon, 8 in the patient's aorta, connected to a controller 9, which in turn connects to an extracorporeal aortic bypass blood pump 10. The occluding device 8 can be any device that can be remotely opened and closed, either partially or fully, but in the preferred embodiment is a balloon. U.S. Pat. Nos. 5,894,273 and 6,137,416 disclose a limited-use controller that does not control an intra-aortic valve, such as the balloon 8. Such a controller could be used to control the aortic bypass blood pump 10. The deflated balloon 8 is mounted on the end of a flexible catheter 11. The balloon 8 and catheter 11 are inserted into the aorta via a peripheral artery, preferably at a point 12 on the femoral artery. The catheter 11 may be inserted percutaneously over a guide wire or surgically by direct exposure of the vessel. The balloon 8 is positioned in the descending thoracic aorta at approximately the level of the diaphragm. More specifically, the balloon 8 is placed above the diaphragm, but below the subdlavian artery.

Figure 2:
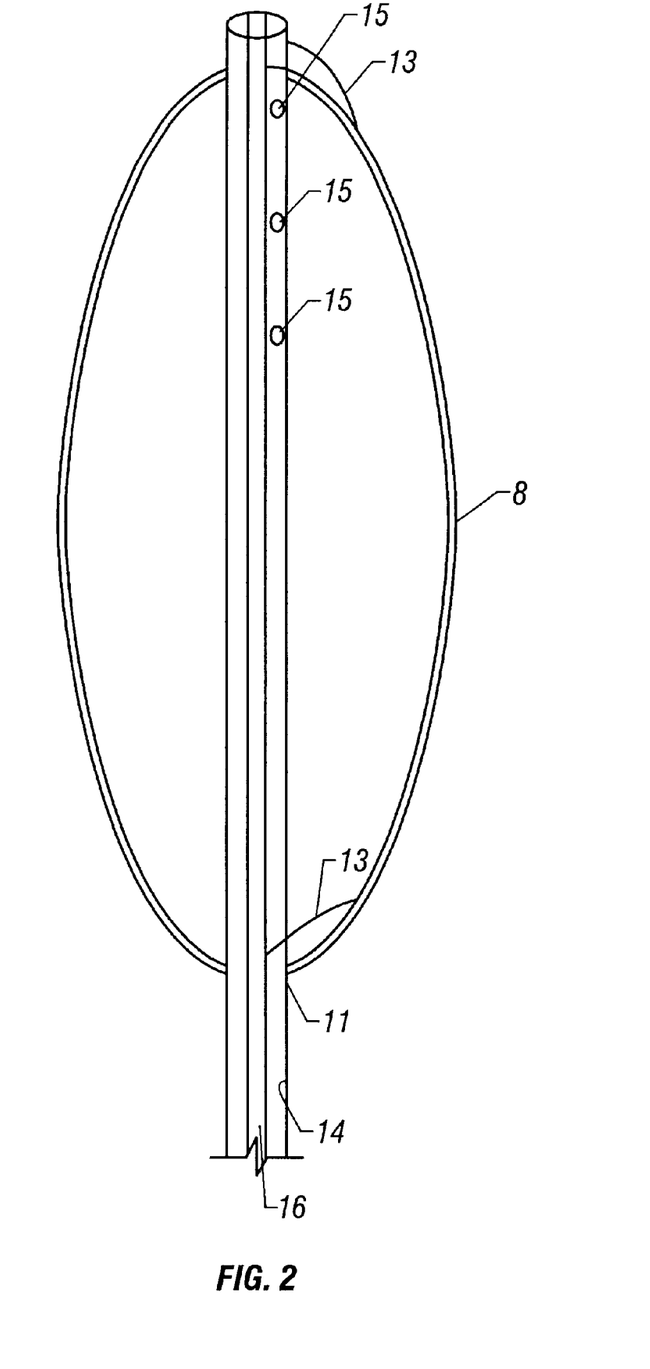
FIG. 2 is a detailed view of the intra-aortic balloon and associated catheter, illustrating some of their features.

Referring now to FIG. 2, the aortic blood pressure AoP is recorded with two pressure transducers, or sensors 13 on the balloon 8. The pressure transducers 13 are conventional transducers, such as model number BP01, manufactured by the InvenSys Company located in Milpitas, Calif. The controller 9 allows sustained flow to pump and reads upper and lower pressure for pump adjustments from the balloon sensors 13. The balloon sensors 13 monitor pressure, and when pressure goes up then pump flow increases, and vice versa. The principle of the balloon 8 is to equalize pressure during systole, and to auto-regulate the flow rate of the pump 10, based on the pressure sensed by the pressure sensors 13 on either side of the balloon 8. The balloon 8 inflates as the aortic valve opens and deflates upon closure. If timed properly, there should be no period in which the aortic valve is closed and the balloon 8 inflated. In an alternate embodiment, only one sensor 13 is used.

The catheter 11 has duel lumens. A larger lumen 14 is used to shuttle gas to and from the balloon 8 via openings or ports 15 located on a catheter wall. A smaller lumen 16 runs continuously through the body of the catheter 11. The smaller lumen 16 is used for inserting the catheter 11 over an aortic guide wire and as a pressure transmission tube for the continuous measurement of central aortic pressure AoP proximal to the balloon 8 during operation of the heart-assist system 10. The balloon 8 and catheter 11 are made of biocompatible polymeric materials. The balloon 8 and catheter 11 are flexible and nontraumatic to the aorta, but have a wall thickness and strength sufficient to withstand cyclic rapid balloon inflation and deflation.

The pressure transducers 13 connect to the pressure transmission tube lumen 16. The lumen 16 couples to a cable 18 that connects to the controller 9. The balloon 8 is inflated and deflated by gas pressure, preferably using helium gas, supplied through a pneumatic tube 20 attached to the large lumen 14. The tube 20 connects to the controller 9. The balloon 8 deflates when depressurized with gas, and inflates when pressurized with gas, thereby partially or fully occluding the aorta. To avoid stagnation of the blood and vessel trauma, the balloon 8 does not need to completely occlude the descending aorta; it may leave some space on either side.

Figure 3A:
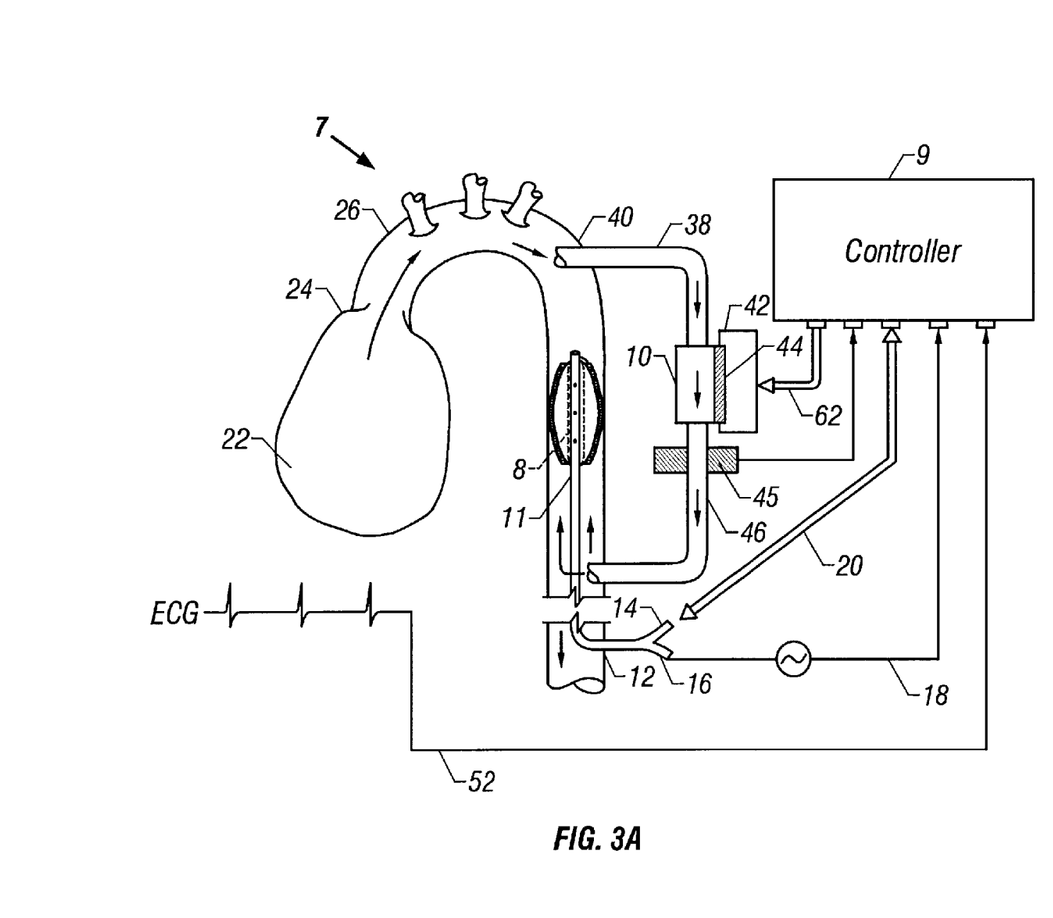
FIG. 3A is a schematic of the temporary heart-assist system, illustrating the intra-aortic balloon, aortic-aortic external bypass pump, and external controller, as installed on a patient.

Referring now to FIG. 3A, the left ventricle 22 of the heart is shown in systole with ejection of blood (long arrow) through the opened aortic outflow valve 24 into the ascending aorta 26. An inlet cannula 38 for the pump 10 is inserted into the aorta at a point 40 proximal to the balloon 8, using conventional surgical techniques. The point 40 may be in the ascending aorta 26, for patients who have an open chest, or may be in a branch vessel, preferably the subclavian artery, for patients whose chest is not open, or at any point between.

Figure 3B:
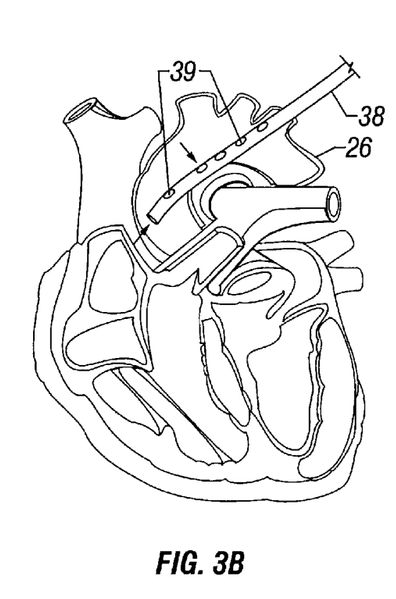
FIG. 3B is a schematic of a human heart, depicting part of an inlet catheter with the tip of the catheter positioned through the aortic valve into the left ventricle.

Referring now to FIG. 3B, in an alternate embodiment, the length of the inlet cannula 38 extends with its tip positioned through the aortic valve 24 into the left ventricle 22. Holes 39 along the length of the inlet cannula 38 in the aorta, combined with a hole 39 in the tip of the cannula 38, provide direct unloading of the left ventricle 22, plus afterload reduction in the aorta.

The lumen of the inlet cannula 38 is of sufficient size and capacity to allow flow rates (see arrow) up to 7 liters per minute, with minimal pressure drop and blood destruction hemolysis. U.S. Pat. No. 6,007,478 discloses a cannula having constant wall thickness with increasing distal flexibility. The full disclosure of this patent is incorporated herein by this reference. The inlet cannula 38 is brought out of the patient and connected to the pump 10. The pump 10 is a commercially available non-pulsatile blood pump. Artificial heart pumps can be classified into the diaphragm type, the tube type, the roller pressure type, and the radial flow type that operates by rotational motion. Typical of the radial flow type is the centrifugal type. The following U.S. Patents disclose centrifugal heart pumps:

U.S. Pat. No. 5,894,273 Centrifugal blood pump driver apparatus

U.S. Pat. No. 6,015,434 Artificial heart pump

U.S. Pat. No. 6,137,416 Method of controlling centrifugal pump

U.S. Pat. No. 6,227,817 Magnetically-suspended centrifugal blood pump

The full diclosures of these patents are all incorporated herein by this reference. The pump 10 may be any radial pump, but in the preferred embodiment the pump 10 is a centrifugal pump. A drive motor 42 powers the pump 10 via a magnetic coupling 44 located between the drive motor 42 and the pump 10. The pump 10 has the capacity to pump up to 7 liters per minute of blood without increased hemolysis or thrombosis clot formation. Pump flow rate is continuously measured using a conventional flow transducer 45 connected to the controller 9. The transducer 45 may be of the ultrasonic or electromagnetic type, but in the preferred embodiment is an ultrasonic model, made by ransonic Systems, Inc., located in Ithaca, N.Y. Blood returns to the patient via an outlet cannula 46 inserted in an infradiaphragmatic artery at a point 48 far from the balloon 8, using conventional surgical techniques. Preferably, the point 48 is in the femoral artery. The lumen of the outlet cannula 46 is of sufficient size and capacity to allow flow rates up to 7 liters per minute, with minimal pressure drop and hemolysis.

An electrocardiogram ("ECG") is recorded via electrodes 50 placed on the skin of the patient. The electrodes couple to cables 52 that connect to the controller 9.

The pump drive motor 42 couples to the controller 9 via a cable 62. The purpose of the pump 10 is to pump blood from the upper arterial compartment 14 to the lower arterial compartment. During ventricular systole, and using the ECG and aortic pressure-triggered controller 9, the small-volume balloon 8 is rapidly inflated, partially occluding the aorta. In the preferred embodiment, the flow rate of the pump 10 is regulated to obtain a specific end-systolic AoP in the upper arterial compartment (aorta 26). However, in an alternate embodiment, the pump runs continuously at a set speed. A deceased end-systolic aortic pressure afterload results in an increase in cardiac output blood flow. Decreased afterload also reduces the workload and oxygen consumption of the failing heart. Increased systemic blood flow also elevates perfusion pressure in the lower arterial compartment. During ventricular diastole, the balloon 8 rapidly deflates, thereby increasing the perfusion pressure throughout the arterial compartment 26. The pump flow rate can also be slowed during diastole by coasting or braking the motor 42, thereby reducing the potential for blood trauma hemolysis. Decreasing pump flow may be obtained by coasting or braking the speed of the centrifugal pump motor. In an alternate embodiment, the pump 10 runs continuously at a set speed.

Figure 4:
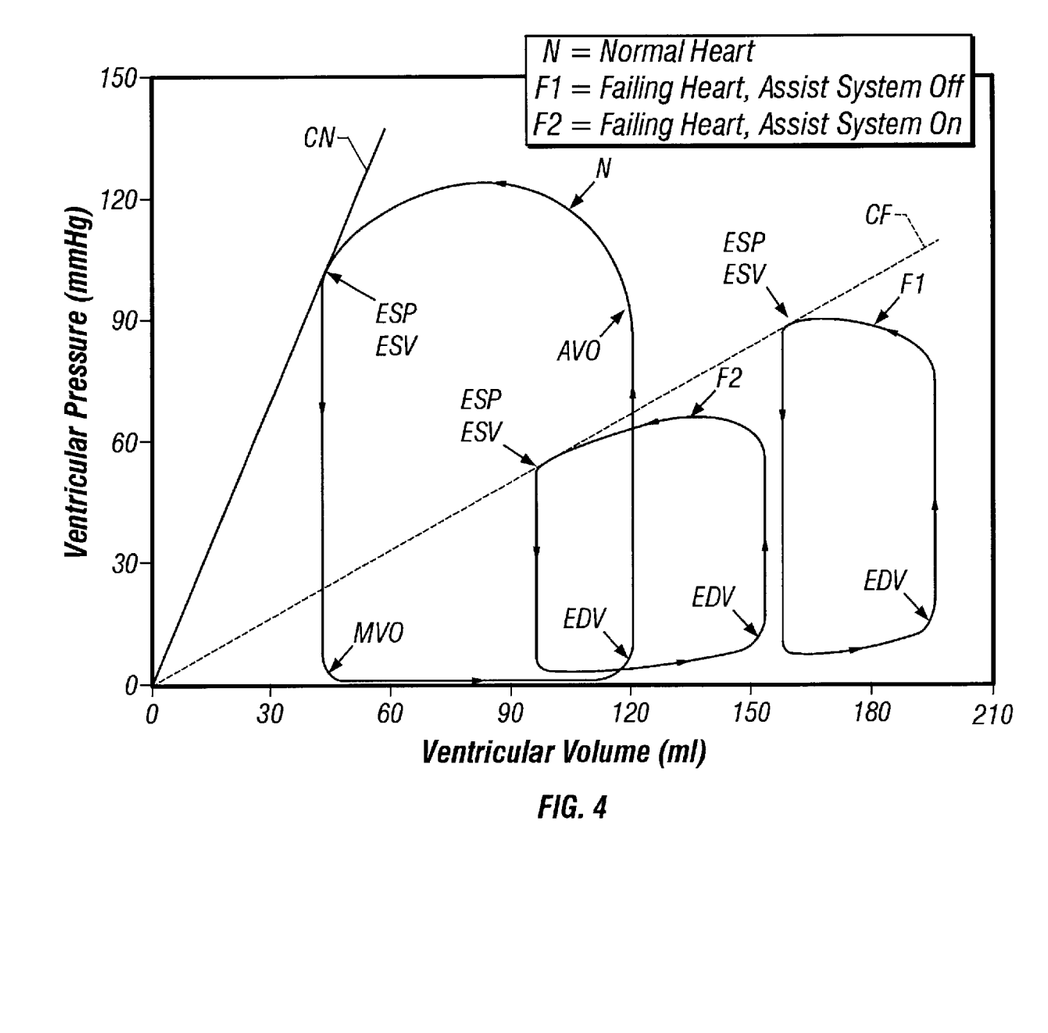
FIG. 4 is a graph of the left ventricular-pressure-volume-contractility relationships for the normal heart, failing heart, and failing heart supported with the temporary heart-assist system according to the present invention.

Referring now to FIG. 4, the y-axis shows ventricular pressure 0–120 mmHg, and the x-axis shows ventricular volume 0–210 ml. An example of the pressure-volume relationship is shown for the normal N heart. Starting at the ventricular end-diastolic volume EDV for the normal heart N, the loop moves in a counter-clockwise direction. First the ventricle contracts and generates pressure sufficient to open the aortic valve AVO. The ventricle ejects blood into the aorta and the ventricular volume decreases. The ventricular stoke volume for each cardiac cycle is calculated by the formula: stoke volume ml/beat =EDV−ESV. At end-systole the aortic valve closes and pressure decreases as the walls of the ventricle relax during diastole. Following opening of the mitral valve MVO the left ventricle fills from the left atrium, containing oxygenated blood from the lungs, and ventricular volume increases. Contractility strength of contraction of the normal ventricle may be defined by the slope of the end-systolic pressure ESP-volume ESV relationship shown as solid line CN. Thus, for a given EDV, cardiac stroke volume decreases with increasing ESP and ESV. Conversely, stroke volume increases with decreasing ESP and ESV for a given EDV and contractility slope. With acute heart failure, the pressure-volume loop F1 is shifted downward and to the right. For this heart failure example, the contractility slope shown as dashed line CF is reduced and the EDV is increased. Despite the increase in EDV and decrease in ESP, the cardiac stroke volume is reduced due to decreased contractility slope. Because of the decreased contractility slope, the ventricle is more sensitive to changes in the ESP. Otherwise stated, with heart failure small changes in ESP lead to larger changes in ESV compared to the normal ventricle.

FIG. 4 also illustrates the effects of the embodiments of the present invention on the failing heart. With actuation of the aortic balloon 8 and the aortic-aortic bypass pump 10, the left ventricle is pressure and volume unloaded. During ventricular systole, the aortic balloon 8 is inflated, occluding the aorta, and the bypass blood pump 10 transfers blood from the upper arterial compartment to the lower arterial compartment. Pump flow rate is controlled increased or decreased to result in a set ESP level. Compared to the unassisted condition loop F1, the reduced ESP during mechanical assistance results in a reduced ESV loop F2 despite an unchanged contractility slope dashed line CF. Thus, reducing ESP and ESV with the heart-assist system 7 will increase cardiac stroke volume systemic perfusion and may also decrease ventricular EDV. Pressure and volume unloading of the ventricle also decreases systolic ventricular wall tension a primary component of cardiac muscle oxygen consumption.

The aortic balloon 8 and aortic bypass pump 10 (axial or centrifugal flow device) are synchronously operated using the ECG-triggered and pressure-feedback controller 9. During ventricular systole the small-volume balloon 8 is rapidly inflated, partially occluding the aorta. The flow rate of the aortic bypass blood pump 10 is regulated to obtain a specific end-systolic aortic pressure in the upper arterial compartment. A decreased end-systolic aortic pressure provided by the blood pump results in ventricular unloading and augmentation of systemic perfusion (stroke volume and cardiac output). The pump 10 assumes the circulation to the lower half of the body and the weakened heart is responsible for the upper half of the body only. Decreased afterload also reduces the workload on the failing heart. The increased systemic blood flow elevates perfusion pressure in the lower half of the body. During ventricular diastole, the balloon is deflated and the pump-generated pressure and flow increases the perfusion pressure throughout the arterial tree. Compared to the prior art intra-aortic balloon pumps, the invention provides greater augmentation of systemic perfusion, improved direct ventricular unloading, and increased diastolic perfusion, and without direct cannulation of the left ventricle or atrium as required for cardiac bypass devices.

Because of aortic occlusion, the pump 10 flows from high pressure to lower pressure and will actually assume about 60% of the work. It is important to note that the pump 10 makes diastole become active. The pump 10 achieves systolic unloading by augmenting flow and increased blood flow during diastolic which reduces load to the heart.

Figure 5A:
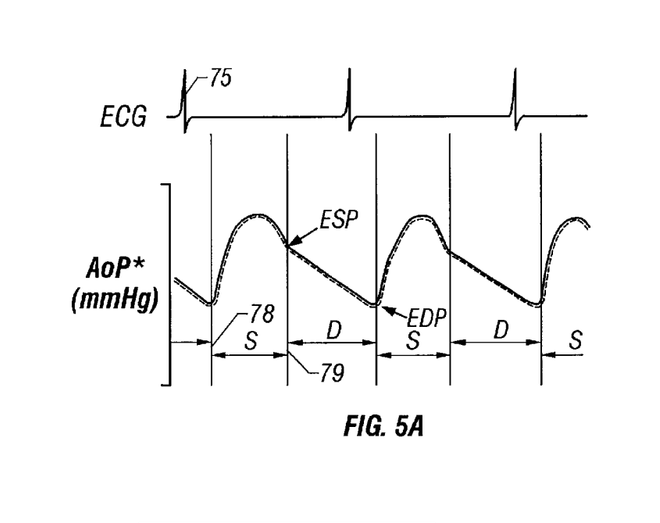
FIG. 5A is a graph showing the electrocardiogram and aortic blood pressures of the failing heart.
Figure 5B:
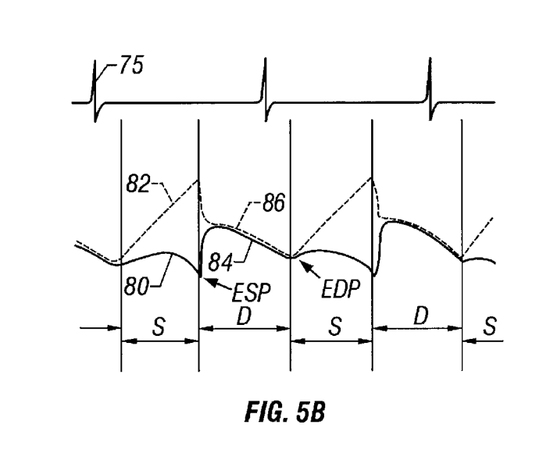
FIG. 5B and FIG. 5C are graphs showing the electrocardiogram, aortic blood pressures, aortic balloon inflation/deflation timing, and bypass pump flow rate or motor speed with the temporary heart-assist system operating.

FIG. 5A and 5B illustrate the functioning of the heart-assist system 7. FIG. 5A shows the ECG and AoP for the heart failure condition with the assist system 7 off. The ECG is recorded from skin electrodes appropriately placed on the patient. The R-wave 75 of the ECG corresponds with the start of ventricular systole and is used as a control trigger. The AoP shows the pressure recorded in the proximal aorta solid line and distal aorta dashed line. With the assist system off and the aortic balloon deflated, the proximal and distal aortic pressures are essentially equal. The start of systole 78 corresponds with the EDP time. The end of systole 79 corresponds with the ESP time. The systolic period S is when left ventricular ejection into the aorta occurs. The diastolic period D is when the ventricle relaxes and coronary perfusion occurs.

Figure 5C:
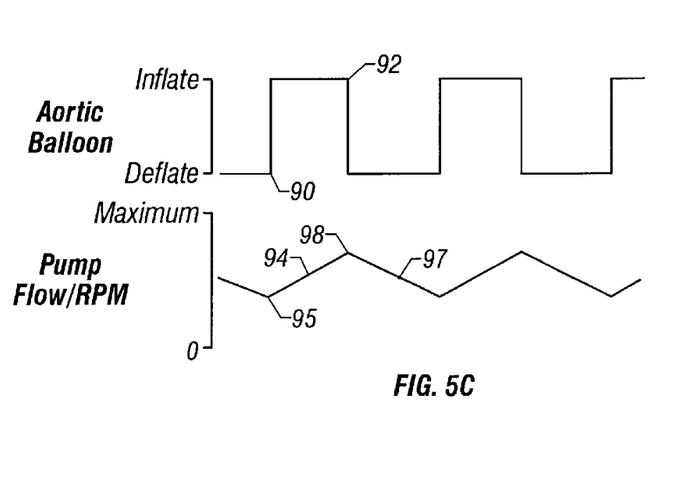

Referring now to FIG. 5B and FIG. 5C, with the heart assist system 7 on, the aortic balloon is activated in two stages: inflation during ventricular systole S and deflation during cardiac diastole D. As shown in FIG. 5B and FIG. 5C, the R-wave of the ECG is used to trigger balloon inflation. The start of balloon inflation 90 is controlled to obtain a preset EDP level measured in the proximal aorta using the pressure transmission lumen 16 of the aortic catheter 11. During inflation the balloon 8 makes uniform and firm contact with the inside wall of the aorta. This has the effect of blocking the downstream flow of blood in the aorta during systole. Thus, a closed volume is created between the outflow valve of the ventricle and the expanded balloon 8.

At the time of systolic S balloon inflation 90, the aortic bypass pump shunts blood from the upper arterial compartment proximal aorta to the lower arterial compartment distal aorta. The centrifugal blood pump flow rate and RPM are regulated by the external controller 9 to obtain a preset ESP level measured in the aorta proximal to the inflated balloon. Thereby, the proximal aortic pressure is decreased solid line 80 and the distal aortic pressure is increased dashed line 82 during systole S compared to the unassisted condition shown in FIG. 5A. At the end of systole start of diastole, the aortic balloon is rapidly deflated 92. Thus the aorta is opened between the upper and lower arterial compartments, and the two pressures equilibrate. The equilibration results in increased proximal solid line 84 and distal dashed line 86 aortic pressures during diastole D compared to the unassisted condition illustrated in FIG. 5A. Therefore, the heart-assist system described in the present invention is capable of increasing cardiac stroke volume and systemic perfusion, reducing ventricular workload and oxygen consumption, and increasing perfusion pressure to the coronary arteries supplying the heart. Also shown in FIG. 5B and FIG. 5C, the flow rate and RPM of the centrifugal aortic-aortic bypass pump may be increased 94 at the time to correspond 95 with aortic balloon inflation 90. This provides for maximum pressure and volume unloading of the ventricle 80 and augmentation of distal perfusion pressure 82. Additionally, the flow rate and RPM of the centrifugal blood pump may be decreased 97 at the time to correspond 98 with aortic balloon deflation 92. The reduced flow rate may decrease the degree of pump-induced hemolysis.

Figure 6A:
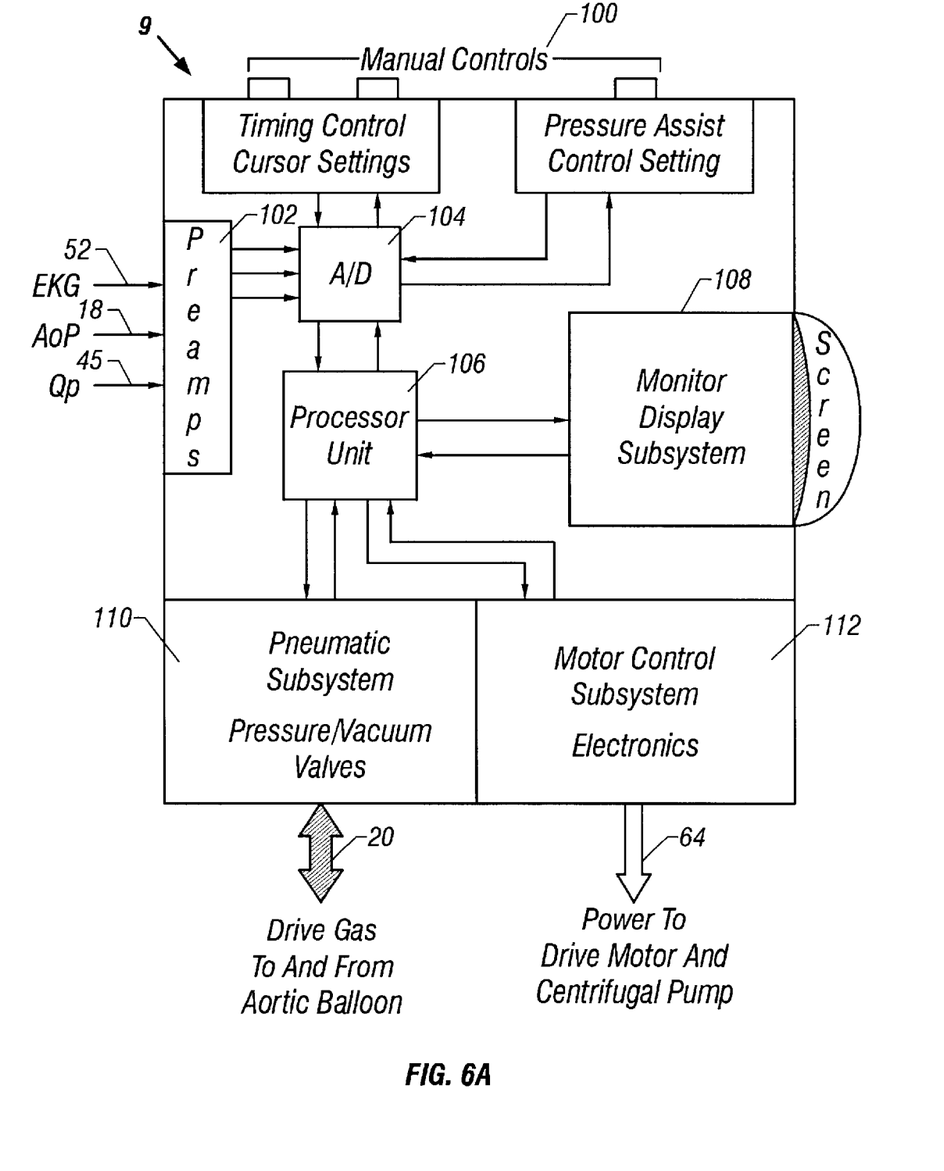
FIG. 6A is a schematic of the external control unit illustrating manual controls, transducer inputs, monitor display, aortic balloon pneumatics, and bypass pump electronics.

FIG. 6A illustrates the components of the heart-assist system control unit 9. Manual controls 100 are used to set the timing of balloon inflation and deflation, and to set the degree of pressure assist provided by the centrifugal blood pump. The control unit contains preamplifiers 102 with EKG 52, aortic pressure 18, and pump flow 45 inputs. Control setting and transducer signals are passed through an A/D converter 104 with before being sent to the processor unit 106 and monitor display subsystem 108. Based on transducer signals and control settings, the processor unit controls and monitors the pneumatic subsystem 110 that provides gas pressure and vacuum to inflate and deflate the aortic balloon, respectively, via a pneumatic drive line 20. Processor unit 106 contains a microprocessor such as a Motorola 68HC11 random access memory (RAM) and program memory (PROM) which contains software to control the'system. The processor unit also controls and monitors the motor control subsystem 112 that sends power to the centrifugal blood pump drive motor via a electronic cable 64.

Figure 6B:
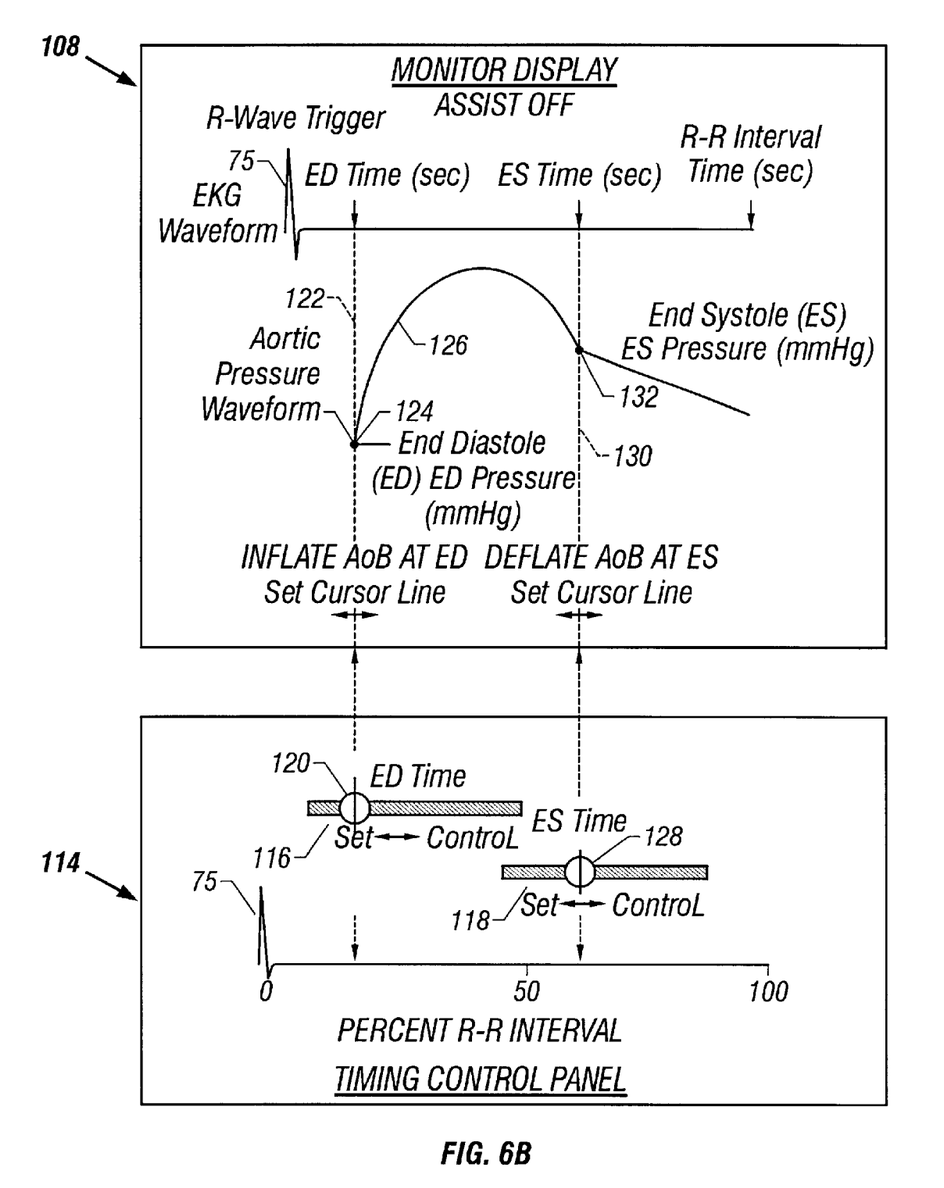
FIG. 6B is a schematic of the assist timing control panel, illustrating the method for setting the inflation and deflation timing of the aortic balloon.

FIG. 6B illustrates the timing control panel 114, on the external control unit, that is used for setting aortic balloon AoB inflation 116 and deflation 118 timing with respect to the R-wave of the electrocardiogram 75 as a percentage of the R-R time interval. With the assist pump and balloon turned off, the aortic balloon inflation time is established by manually moving the slide control 120 that controls a cursor line 122 simultaneously shown on the monitor display 108. The slide control is moved such that the cursor line corresponds with end-diastole ED and the ED pressure 124 overlying the displayed aortic pressure waveform 126. Additionally, balloon deflation time is established by manually moving the slide control 128 that controls a second cursor line 130 on the display monitor. The slide control is moved such that the cursor line corresponds with end-systole ES and the ES pressure 132 for the aortic pressure waveform. In the event that heart rate changes by +10 beats per minute, the assist pump and balloon should be turned off and the inflation and deflation timing reestablished.

Figure 6C:
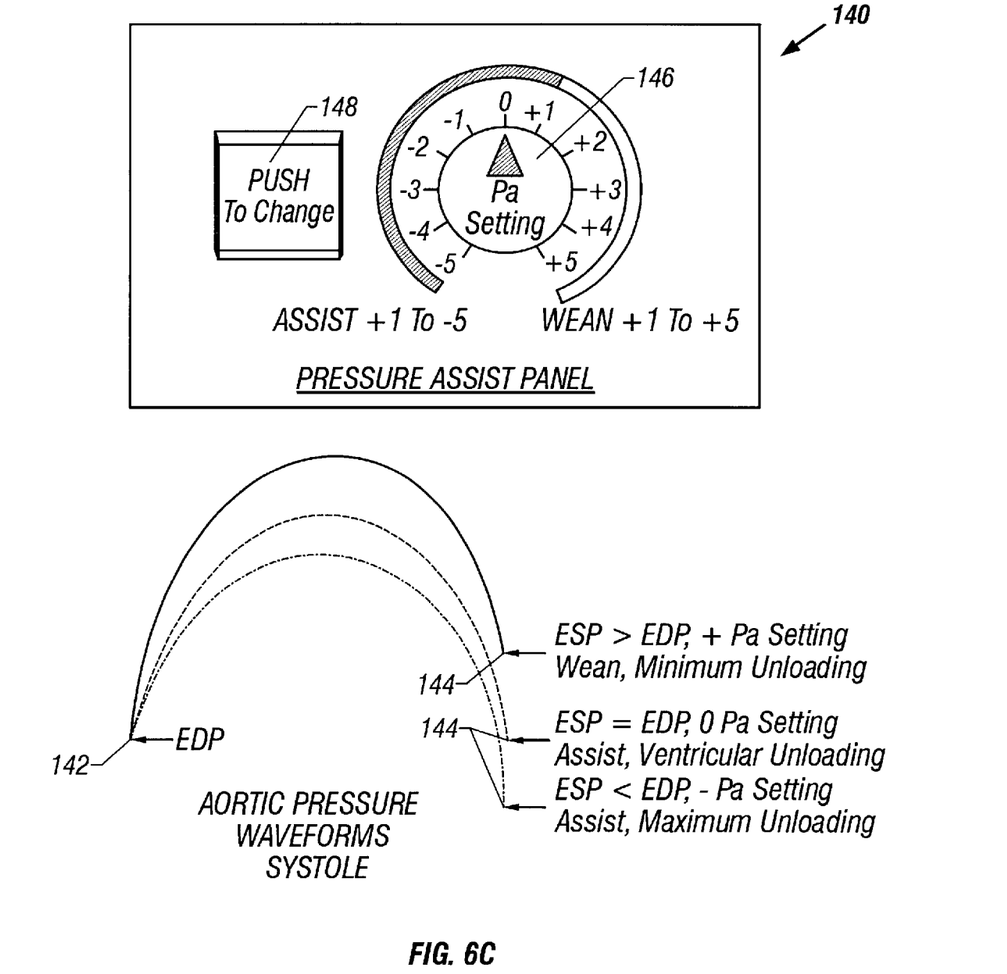
FIG. 6C is a schematic of the pressure assist control panel, illustrating the method for setting the degree of systolic pressure unloading of the heart.

FIG. 6C illustrates the pressure assist Pa control panel 140, on the external control unit, that is used for setting the degree of ventricular unloading provided by the aortic bypass pump. The degree of ventricular unloading is determined by the measured difference between the aortic end diastolic pressure EDP 142 and the end systolic pressure ESP 144. A control knob 146 is manually set to establish the degree of pressure unloading which ranges from a negative 5 mmHg to a positive 5 mmHg. A control knob setting of 0 corresponds with the ESP=EDP. This setting provides a moderate level of ventricular unloading and heart assist. A setting of −5 corresponds with the ESP being 5 mmHg less than the corresponding EDP. This setting provides the maximum level of ventricular unloading and heart assist. A setting of +5 corresponds with the ESP being 5 mmHg more than the EDP. This setting provides the minimum level of ventricular unloading and is used for weaning from the heart assist system. The illustrated control method allows for beat-to-beat control of pump flow rate regardless of changes in the systemic vascular resistance and blood pressure. A manual push button 148 must be depressed simultaneously with changing the control knob setting. This method is used to prevent inadvertent changes in the pressure assist setting.

Figure 6D:
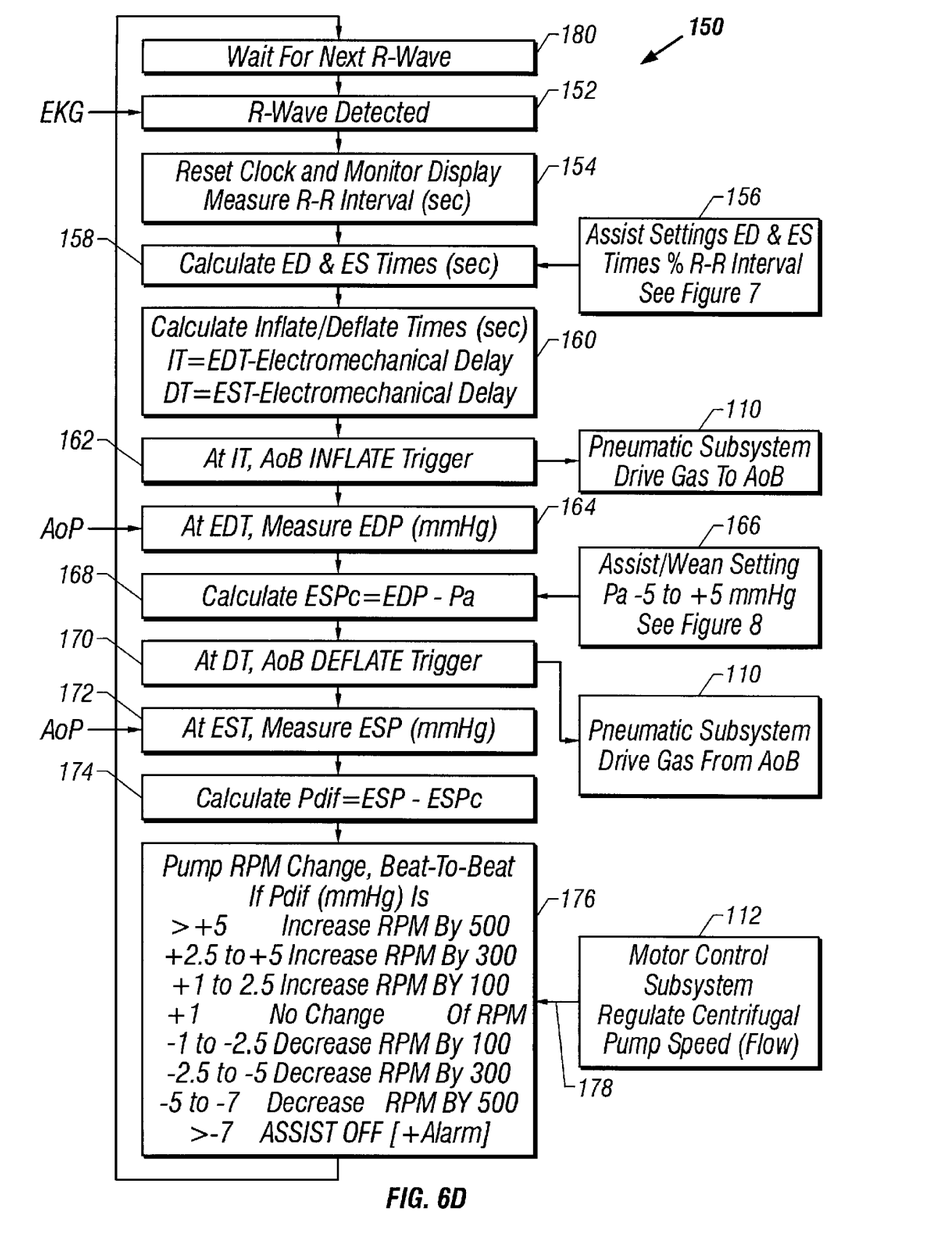
FIG. 6D is a detailed graph showing the control-logic loop for the heart assist system.

FIG. 6D is a detailed flow diagram of the heart-assist system control logic 150. Beat to beat control of the aortic occlusion balloon and aortic bypass pump is started with electrocardiogram R-wave detection 152. With R-wave detection the timing clock and monitor displays are reset and the preceding R-R interval time is measured 154. Based on the percentage ED and ES control setting 156 shown in FIG. 7, the ED and ES times in seconds is calculated 158 for the measured R-R interval 154. Aortic balloon inflation IT and deflation DT times 160 are calculated by subtracting a known electromechanical delay time for the pneumatic subsystem from the previously calculated ED and ES times 158, respectively. At the calculated balloon inflation time IT following R-wave detection, a trigger signal 162 is sent to the pneumatic subsystem 110 to provide drive gas to the aortic balloon. At the calculated ED time, the ED pressure EDP is measured 164 from the aortic pressure input signal. Based on the pressure assist control setting shown in FIG. 8, the calculated ES pressure ESPc 168 is determined using the formula: ESPc=measured EDP 164 minus the pressure assist Pa setting 146. At the calculated balloon deflation time DT following R-wave detection, a trigger signal 170 is sent to the pneumatic subsystem 110 to exhaust drive gas from the aortic balloon. At the calculated ES time, the ES pressure ESP is measured 172 from the aortic pressure input signal.

The calculated pressure difference Pdif 174 is determined using the formula: Pdif=measured ESP 172 minus the calculated ESPc 168. The bypass pump speed RPM change is determined 176 based on the calculated Pdif 174. Positive Pdif values result in increasing pump speeds. Conversely, negative Pdif values result in decreasing pump speeds. A speed control change signal 178 is sent to the motor control subsystem 112 which regulates centrifugal pump flow. Following the above steps, the control logic unit waits for the next R-wave detection 180.

Thus, the invention provides a method and apparatus for assisting the failing heart until such time that ventricular recovery and weaning from the assist system occurs. There are several advantages of this invention over prior intra-aortic balloon pump and ventricular assist devices. The invention is particularly useful in increasing cardiac output and decreasing ventricular loading without direct cannulation of the left atrium or left ventricle. The method includes controlled intermittent occlusion of the aorta synchronously with the cardiac cycle, accompanied by the pumping of blood from the proximal to the distal aorta at a rate sufficient to pressure and volume unload the failing left ventricle. Systolic ventricular unloading increases cardiac output and decreases myocardial oxygen demands. Augmented cardiac output levels also increase perfusion of the coronary arteries supplying oxygenated blood to the heart.

From the foregoing detailed description, it is apparent that the present invention provides a method and apparatus for mechanically assisting the failing heart. It should be understood that the invention is not intended to be limited to the specifics of the described preferred embodiments, but is defined by the accompanying claims.

What is claimed is:

1. A temporary heart-assist system comprising:
   a. an occluding device positonable in a patent's descending aorta, the occluding device having a pressure sensor;
   b. an extra-corporeal controller electrically connectable to ECG electrodes and to the pressure sensor, and coupled to the occluding device;
   c. an extra-corporeal pump electrically coupled to the extra-corporeal controller, the pump having an inlet connectable to a patent's supra-diaphragmatic artery, and having an outlet connectable to the patient's infra-diaphragmatic artery, the pump when operating having RPM's and a flow rate.

2. The temporary heart-assist system of claim 1, wherein the ECG electrodes are adapted to sense a patient's cardiac cycle, and to generate a sensed ECG signal in reponse to the patient's cardiac cycle, and wherein the extra-corporeal controller is adapted to a) cause the occluding device to intermittently occlude the aorta, syncronously with the sensed ECG signal, and b) cause the extra-corporeal pump to pump blood at a rate sufficient to pressure and volume unload the patient's failing left ventricle.

3. The temporary heart-assist system of claim 2, wherein the extra-corporeal controller decreases the flow rate and RPM's of the extra-corporeal pump when the extra-corporeal controller opens the occluding device.

4. The temporary heart-assist system of claim 3, wherein the pump is an axial flow pump.

5. The temporary heart-assist system of claim 4, wherein the pump is a centrifugal flow pump.

6. A temporary heart-assist system comprising:
   a. a balloon positonable in a patient's descending aorta, the balloon having two pressure sensors;
   b. an extra-corporeal controller electrically connectable to ECG electrodes and to the two pressure sensors, and pneumatically coupled to the balloon;
   c. an extra-corporeal pump electrically coupled to the extra-corporeal controller, the pump having an inlet connectable to a patient's supra-diaphragmatic artery, and having an outlet connectable to the patients infra-diaphragmatic artery, the pump when operating having RPM's and a flow rate.

7. The temporary heart-assist system of claim 6 wherein the ECG electrodes are adapted to sense a patient's cardiac cycle, and to generate a sensed ECG signal in reponse to the patient's cardiac cycle, and wherein the extra-corporeal controller is adapted to a) cause the balloon to intermittently occlude the aorta, synchronously with the sensed ECG signal and b) cause the extra-corporeal pump to pump blood at a rate sufficient to pressure and volume unload the patient's failing left ventricle.

8. The temporary heart-assist system of claim 7, wherein the extra-corporeal controller decreases the flow rate and RPM of the extra-corporeal pump when the extra-corporeal controller deflates the baloon.

9. The temporary heart-assist system of claim 8, wherein the pump is an axial flow pump.

10. The temporary heart-assist system of claim 9, wherein the pump is a centrifugal flow pump.

11. The temporary heart-assist system of claim 10, wherein the inlet connectable to a patent's supra-diaphragmatic artery is an inlet cannula, connectable through an aortic valve into the left ventricle, the inlet cannula having holes along a length of the inlet cannula, positionable in the aorta, and a hole in a tip, which is positionable in the left ventricle, for providing direct unloading of the left ventricle, and after-load reduction in the aorta.

* * * * *

UNITED STATES PATENT AND TRADEMARK OFFICE
CERTIFICATE OF CORRECTION

PATENT NO. : 6,669,624 B2
DATED : December 30, 2003
INVENTOR(S) : Frazier It is certified that error appears in the above-identified patent and that said Letters Patent is hereby corrected as shown below:

<u>Title page,</u>
Item [76], should read -- O. Howard Frazier,. Cardiovascular Therapies, Inc., c/o J.F. Brazos Enterprises, Ltd., 1932 Norfolk, Houston, Tx. (US) 77098 --
Item [57], ABSTRACT,
Line 9, should delete second instance of "artery".

Signed and Sealed this

Sixth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,669,624 B2
DATED : December 30, 2003
INVENTOR(S) : O. Howard Frazier It is certified that error appears in the above-identified patent and that said Letters Patent is hereby corrected as shown below:

<u>Title page,</u>
Item [57], ABSTRACT,
Line 8, after "diaphragmatic" insert -- artery --.

Signed and Sealed this

Fifteenth Day of June, 2004

JON W. DUDAS
*Acting Director of the United States Patent and Trademark Office*